US00PP29549P2

(12) United States Plant Patent
Hansen

(10) Patent No.: US PP29,549 P2
(45) Date of Patent: Jul. 24, 2018

(54) ***MONARDA* PLANT NAMED 'BLUE MOON'**

(50) Latin Name: ***Monarda* hybrid**
Varietal Denomination: Blue Moon

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 40 days.

(21) Appl. No.: 15/530,506

(22) Filed: Jan. 23, 2017

(51) Int. Cl.
*A01H 5/02* (2018.01)

(52) U.S. Cl.
USPC ..... Plt./455

(58) Field of Classification Search
USPC ..... Plt./263.1, 455
See application file for complete search history.

(56) References Cited

PUBLICATIONS

Walters Garden's 2016-2017 Catalogue. https://www.provenwinners.com/sites/provenwinners.com/files/catalogs_pdfs/1-26_front_pages.pdf. 5 pages.*

* cited by examiner

*Primary Examiner* — Susan McCormick Ewoldt
*Assistant Examiner* — Karen M Redden

(57) ABSTRACT

The new and distinct cultivar of ornamental cultivar of bee balm plant named *Monarda* 'Blue Moon' has compact, clumping habit with short rhizomes, basally branching stems, medium to dark green foliage with slight tinting of greyed purple, numerous large lavender blue-colored flowers creating excellent flower coverage and foliar resistance to powdery mildew. 'Blue Moon' may rebloom in early fall if cut back hard. The new plant is useful for landscaping in containers or in the ground, as accent plants or en masse.

1 Drawing Sheet

Botanical classification: *Monarda* hybrid.
Variety denomination: 'Blue Moon'.

BACKGROUND OF THE INVENTION

The present invention relates to the new and distinct cultivar of bee balm plant, botanically known as *Monarda* 'Blue Moon', and hereinafter also referred to solely as the cultivar 'Blue Moon' or the "new plant". The new plant was selected from seed collected by the hybridizers on Aug. 9, 2012 from a selfing made on Jun. 12, 2012 at the hybridizing plot of a wholesale perennial nursery in Zeeland, Mich., USA, between the proprietary unreleased, not patented hybrid known as H10-26-07 as the female or seed parent as well as the male or pollen parent. The plant was a single selection originally made in the summer of 2014 from the batch of seeds sown in the fall of 2012. Further selection was completed in the trial fields of the same nursery in Zeeland, Mich. in the summer of 2015 and the plant was assigned the breeder code of H12-62-3. The plant has been asexually propagated by shoot tip cuttings since in 2014 at the same nursery in the greenhouses in Zeeland, Mich., and the subsequent asexually propagated plants have been found to be stable, true to type and identical to the original selection.

No plants of *Monarda* 'Blue Moon' have been sold in this country, or anywhere in the world, under this or any name, prior to the filing of this application, nor has any disclosure of the new plant been made prior to the filing of this application with the exception of that which was sold or disclosed within one year of the filing of this application and was either derived directly or indirectly from the inventors.

BRIEF SUMMARY OF THE PLANT

*Monarda* 'Blue Moon' is unique from its parent and all other bee balm plants known to the inventors. The nearest comparison varieties are 'Pardon My Lavender' U.S. Plant Pat. No. 28,770, 'Leading Lady Plum' U.S. Plant Pat. No. 26,447 and 'Leading Lady Lilac' U.S. Plant Pat. No. 26,431. 'Pardon My Lavender' is slightly shorter with less spreading rhizomes, and the flower color is light lavender pink compared with the lavender blue flower of the new plant. Compared with 'Leading Lady Plum', the new plant is taller, flowering about a week later and the flower color is lavender blue rather than magenta purple. Compared with 'Leading Lady Lilac' the new plant is taller, flowering about one week later and the flower color is lavender blue rather than light lilac purple. Compared with the co-pending U.S. Plant patent application Ser. No. 15/530,505 *Monarda* 'Pink Frosting' the new plant is slightly taller and the flower color is lavender blue rather than pastel pink of 'Pink Frosting'. Compared with the parent, the new plant is shorter and more compact and the flower color is lighter color of lavender blue rather than the rich lavender purple.

The following are traits of *Monarda* 'Blue Moon' that in combination distinguish it from all other bee balm known to the inventor:

1. Winter-hardy, clumping habit with short compact rhizomes.
2. Medium to dark-green lanceolate leaves
3. Newly expanding foliage with tinting of greyed purple.
4. Powdery mildew resistant foliage.
5. Large-sized, lavender blue-colored flowers for a long period in summer with excellent flower coverage.

BRIEF DESCRIPTION OF THE DRAWINGS

The photographs of the new plant demonstrate the unique traits of 'Blue Moon' and the overall appearance of the plant at two-years-old in the full-sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
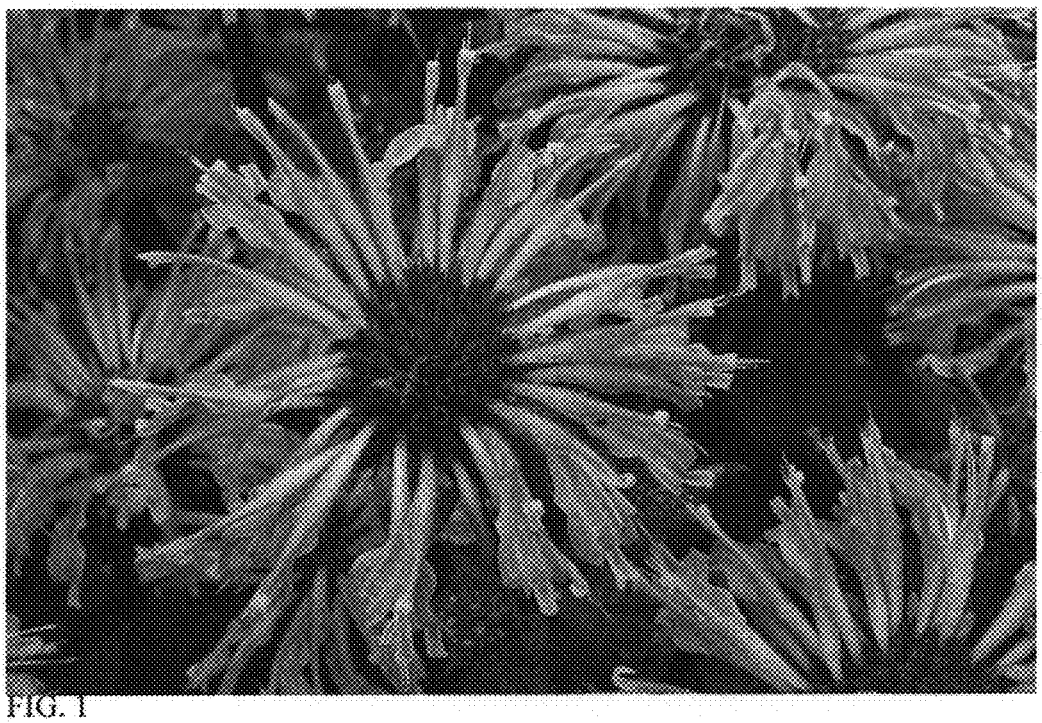
FIG. 1 shows a close-up of the flowers.
Figure 2:
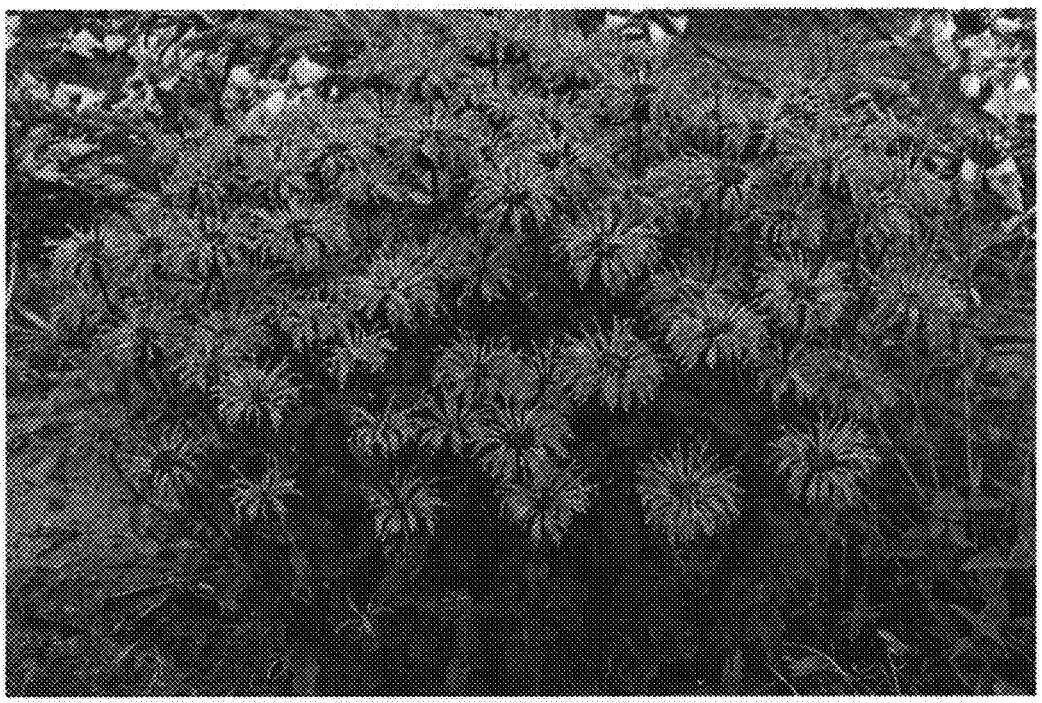
FIG. 2 shows the new plant in flower in the landscape.

The following descriptions and color references are based on the 2001 edition of The Royal Horticultural Society Colour Chart except where common dictionary terms are used. *Monarda* 'Blue Moon' has not been observed under all possible environments. The phenotype may vary slightly with different growing environments such as temperature, light, fertility, soil pH, moisture and maturity levels, but without any change in the genotype. The following observations and size descriptions are based on two-year old greenhouse-grown plants in gallon containers at a nursery in Zeeland, Mich. with supplemental fertilizer and water as needed but without plant growth regulators or pinching.

Botanical classification: *Monarda* hybrid;

Parentage: Female (seed) parent is H10-26-07; male (pollen) parent is H10-26-07;

Plant habit: Winter-hardy herbaceous perennial, compact, producing 12 to 20 stems spreading by short compact rhizomes; to about 50 cm tall at flowering and about 60 cm wide at flower height; flowering begins mid-summer in Michigan and continuing for about 5 to 8 weeks;

Propagation: Stem cuttings;

Time to produce finished crop in 3.8 liter pots: about 10 to 12 weeks; moderate rate of growth;

Root: Fine, fibrous and freely branching; color creamy white to tan depending on soil type;

Leaves: Simple, lanceolate, opposite, serrated, puberulent to pubescent above and below; lustrous above, matte below; acute apex, rounded to cuneate base; to about 8.0 cm long by about 3.6 cm wide, average about 6.5 cm long and 3.0 cm wide;

Leaf color: Young expanding leaves nearest RHS 145C on adaxial surface with tinting of nearest RHS 187A and on abaxial surface nearest RHS 145C; mature adaxial leaves nearest RHS 139A and abaxial surface nearest RHS 137C;

Foliage fragrance: Pleasantly suaveolent, lemony;

Veins: Pinnate; pubescent abaxial with minute puberulent to glabrous adaxial; slightly sunken above and costate below;

Vein color: Young expanding leaves nearest RHS 157A with a tint of nearest RHS 187A, adaxial nearest RHS N186C; mature abaxial vein nearest RHS 145C and adaxial nearest RHS 160D with tinting of nearest RHS 187A;

Bracts: Between distal leaves and flowers; sessile; deltoid to lanceolate, with acuminate apex and truncate base; about seven per terminal verticillaster; average about 1.4 cm long and 1.0 cm wide;

Bract color: Abaxial and adaxial between RHS N186C and RHS 187C;

Petiole: Pubescent abaxial and adaxial, concavo-convex; to about 8.0 mm long and 2.5 mm wide at base; average about 6.0 mm long and 2.0 mm wide;

Petiole color: Abaxial nearest RHS 145C, adaxial nearest RHS 137D along margins with light to strong tinting of nearest RHS 187A in center and bleeding out toward margin on some petioles;

Stems: Quadrangular, sparsely pubescent; about 3.5 mm across at base and about 40 to 48 cm long;

Stem color: Nearest RHS 146D with light tinting of nearest RHS 176B in regions of heavy light exposure;

Lower branches: Quadrangular, puberulent, pubescent; attitude upright; average about four per main stem; about 2.0 mm across at base and up to 35 cm long;

Lower branch color: Same as main stem;

Nodes: About 16 per main stem and 10 on lowest branches; average internode about 3.0 cm, shorter in lower portion; color same as surrounding stem;

Flowers: Single, bilabiate, actinomorphic; arranged in terminal verticillate head about 9.5 cm across and 4.0 cm tall opening from the center and progressing outwardly and down; each flower persisting about 5 days in Michigan; numerous, about 80 flowers per head; inflorescence attitude upright, individual flowers outwardly toward outer portion of verticil to slightly upright in center of verticil; self-cleaning;

Flower period: Usually late June into July; about four to five weeks; may repeat in early fall if deadheaded;

Flower fragrance: Moderately spicy;

Buds one to two days prior to opening: Narrowly oblanceolate; terete; arcuate downward; rounded apex; about 2.3 cm long and about 3.5 mm tall and 2.0 mm across in the middle;

Bud color one to two days prior to opening: Nearest RHS N82A in distal portion with base of nearest RHS 84C;

Petals: Bilabiate, arcuate downward; fused into tube in basal 2.0 cm; upper lip 3.2 cm long and 3.0 mm wide at fusion, curled back 180 degrees in distal 2.0 mm, involute in middle portion, flattened distally, apex acute, pubescent abaxial and glabrous adaxial; lower lip with three apical lobes, center lobe emarginate 1.0 mm deep, 4.0 mm long and 2.0 mm across, two side lobes rounded apex, glabrous adaxial and pubescent abaxial, 1.0 mm long and 2.2 mm across; lower lip 6.5 mm across at fusion of lobes; fused tube portion pubescent abaxial and adaxial from base to rictus;

Petal color: Lower lip abaxial center lobe and middle portion nearest RHS N81C, side lobes nearest RHS N81B; adaxial side lobes nearest RHS N80A and center lobe between RHS N80B and RHS N81B; upper lip abaxial nearest RHS N81B and adaxial nearest RHS N81C; fused tube abaxial base nearest RHS 155D, abaxial distal portion nearest RHS N81D, adaxial base nearest RHS 155D and adaxial distal portion nearest RHS N81D;

Androecium: Four;

*Filaments*.—Adnate to adaxial petal about 14.0 mm from base; two 15.0 mm long and 0.5 mm diameter; two rudimentary about 1.0 mm long and 0.2 mm diameter and without anthers; color distally nearest RHS N80D, proximally white, lighter than RHS 155D.

*Anther*.—Oblong elliptic, dorsifixed, longitudinal; 1.8 mm by 0.5 mm; color nearest RHS 187A.

*Pollen*.—Abundant, elliptic to globose, less than 0.1 mm; color nearest RHS 155D.

Gynoecium: One per flower;

*Style*.—About 3.6 cm by 0.5 mm; color nearest RHS N81B toward distal end, lightening to nearest RHS 155D toward base.

*Stigma*.—Split in two in the distal 1.0 mm, 0.25 mm in diameter; color nearest RHS N81B.

*Ovary.*—1.0 mm by 0.75 mm; color between RHS 143D and RHS 144B.

Sepals: Five, narrowly acute to apiculate apex, base fused in basal 9.0 mm forming calyx about 10.0 mm long and 1.2 mm diameter; apex glandular and with minute hairs on abaxial surface;

Sepal color: Abaxial nearest RHS 145B with tinting of nearest RHS N187A toward apex and veins of nearest RHS 146B; adaxial nearest RHS 145C with veins of nearest RHS 146B and apex of nearest RHS N187A;

Pedicel: Terete; glabrous, about 1.0 mm long and 0.7 mm diameter; color nearest RHS 145B;

Peduncle: Pubescent, stiff, strong, erect, quadrangular to about 3.5 mm across at base and average about 42.0 cm long;

Peduncle color: Nearest RHS 146D with light tinting of nearest RHS 176B in areas of heavy light exposure;

Fruit: Single nutlet, slightly flattened ovoid, about 1.2 mm long and 1.0 mm wide; color nearest RHS 202A;

Hardiness: The new plant grows best with plenty of moisture and adequate drainage; hardy to at least from USDA zone 4 through 9;

Disease and pest resistance: Demonstrated powdery mildew resistance (*Sphaerotheca pannosa* var. *rosa*);

It is claimed:

1. A new and distinct cultivar of ornamental bee balm plant, *Monarda* 'Blue Moon', as herein described and illustrated.

* * * * *